United States Patent [19]

Ishikawa et al.

[11] 4,271,327

[45] Jun. 2, 1981

[54] DEHYDROGENATION OF CYCLOHEXANES

[75] Inventors: Toshio Ishikawa, Tokyo; Shuichi Niwa, Komae; Shoko Yamadaya, Tokyo; Yoshio Orito, Musashino, all of Japan

[73] Assignees: Agency of Industrial Science & Technology; Ministry of International Trade & Industry, both of Tokyo, Japan

[21] Appl. No.: 127,381

[22] Filed: Mar. 5, 1980

Related U.S. Application Data

[62] Division of Ser. No. 20,181, Mar. 13, 1979, Pat. No. 4,221,678.

[30] Foreign Application Priority Data

Sep. 27, 1978 [JP] Japan ............................. 53-118761

[51] Int. Cl.³ ............................................. C07C 5/41

[52] U.S. Cl. .................................... 585/440; 585/434
[58] Field of Search ............................ 585/434, 440

[56] References Cited

U.S. PATENT DOCUMENTS 3,622,503  11/1971  Hausler .......................... 252/477 Q
4,048,245   9/1977  Pollitzer et al. .............. 252/466 P X

*Primary Examiner*—Veronica O'Keefe
*Attorney, Agent, or Firm*—Oblon, Fisher, Spivak, McClelland & Maier

[57] ABSTRACT

A catalyst having a noble metal of Group 8 of the Periodic Table of Elements carried on aluminum sponge and a method for the dehydrogenation of cyclohexanes which comprises bringing cyclohexanes, in a heated state, into contact with the catalyst described above in conjunction with hydrogen.

2 Claims, No Drawings

DEHYDROGENATION OF CYCLOHEXANES

This is a division of application Ser. No. 020,181 filed Mar. 13, 1979, now U.S. Pat. No. 4,221,678 issued Sept. 9, 1980

BACKGROUND OF THE INVENTION

This invention relates to a catalyst for the dehydrogenation of cyclohexane and alkyl-substituted cyclohexanes and to a method for the dehydrogenation of cyclohexane and alkyl-substituted cyclohexanes. For brevity of description, cyclohexane and alkyl-substituted cyclohexanes will be collectively referred to hereinafter as "cyclohexanes."

It has heretofore been known in the art to produce benzene, cyclohexene, toluene, xylene, etc. by dehydrogenating cyclohexanes. This dehydrogenation is an andothermic reaciton. Thus, the large volume of heat discharged from a special chemical or other plant is utilized as a source of heat to be absorbed in the dehydrogenation which converts cyclohexanes into benzene, cyclohexene, toluene, xylene, etc. and hydrogen. In other words, this reaction of dehydrogenation can be effectively utilized for the purpose of capturing heat which would otherwise go to waste as chemical energy capable of being stored and even transported.

In this respect, the dehydrogenation of cyclohexanes has considerable industrial significance. It has been usual practice, for the gaseous-phase dehydrogenation of cyclohexanes, to use aluminum-platinum catalyst (How to Make a More Effective Platinum-Alumina Catalyst, Russell W. Maatman, Industrial and Engineering Chemistry 51 (No. 8), 913–914, 1959; Use of Platinum Group Catalysts in Petroleum and Petrochemical Industries, Tatsuo Yamanaka, Journal of the Japan Petroleum Institute 12 951–955, 1969), chromium-alumina catalyst (The Effects of Potassium on Chromia Catalyst, Sterling E. Volty and Sol W. Weller, J. Phys. Chem. 59 569–571, 1955), molybdenum-alumina catalyst (Heat Stability of Molybdena-Alumina Dehydrocyclization Catalysts, Allen S. Russell and John J. Stokes, Jr., Industrial and Engineering Chemistry 40 520–524 1948) and molybdenum oxide and chromium oxide catalyst (Oxides of the Transition Metals as Catalysts, Alfred Clark, Industrial and Engineering Chemistry 45 1476–1480 1953) which invariably use alumina as a carrier.

It should be noted, however, that alumina has a relatively low thermal conductivity (T/K) of 26.4 at 400° C. and catalysts which use alumina as their carriers consequently possess poor thermal conductivity. Moreover, when the temperatuure of the reaction is elevated above 500° C., a decomposition reaction occurs and the selectivity of the dehydrogenation products such as, for example, benzene and toluene, xylene is severely degraded.

The inventors continued a study in search of a catalyst which is excellent in thermal conductivity and selectivity to dehydrogenation products and, therefore, ideal for use in the dehydrogenation of cyclohexanes. They have consequently accomplished the present invention.

An object of the present invention is to provide a catalyst capable of promoting the dehydrogenation of cyclohexanes and consequently aiding in affording dehydrogenation products in high yields and with high selectivity.

Another object of this invention is to provide a method for the dehydrogenation of cyclohexanes by use of the aforementioned catalyst of the present invention, whereby the dehydrogenation products are obtained in high yields and with high selectivity.

SUMMARY OF THE INVENTION

To accomplish the objects described above according to the present invention, there is provided a catalyst which comprises aluminum sponge and a noble metal of Group 8 of the Periodic Table of Elements carried on the aluminum sponge in a ratio of 0.001 to 0.1 part by weight of the noble metal to 1 part by weight of the aluminum sponge. The reaction of dehydrogenation further contemplated by the present invention comprises heating at least one compound selected from the group of cyclohexanes in conjunction with hydrogen at temperatures in the range of from 290° to 620° C. in the presence of the catalyst described above.

By using the catalyst of the present invention specifically as described above, the dehydrogenation of cyclohexanes can be carried out with high efficiency. Particularly because the aluminum sponge used as the carrier in the catalyst enjoys high thermal conductivity, the dehydrogenation of cyclohexanes advantageously proceeds while the otherwise possible decomposition of cyclohexanes is repressed. The dehydrogenation of cyclohexanes is an endothermic reaction. Thus, the heat released from some other reaction and normally wasted can be utilized advantageously as thermal energy for promoting this hydrogenation. The dehydrogeneration products obtained by the method of this invention may be reconverted into cyclohexanes by the reaction of hydrogenation. In other words, the thermal energy originating in the waste heat mentioned above can be preserved in the dehydrogenation products. Thus, the thermal energy can be converted into chemical energy and preserved in that form.

The other objects and characteristic features of the present invention will become apparent from the detailed description given below.

DESCRIPTION OF THE PREFERRED EMBODIMENT

As the first step, aluminum sponge is prepared. A typical method available for the preparation of aluminum sponge (as disclosed in Japanese Patent Publication Sho-51(1976)-40001) will be described below: Aluminum is melted by heating and the fused aluminum is agitated at 620° to 660° C. to impart thereto an aerated texture resembling sponge. The sponge-like mass of aluminum is molded in the required form and, at the ame time, cooled suddenly. Consequently, there are obtained grains of sponge aluminum.

The aluminum sponge will serve as the carrier in the catalyst and, therefore, is required to possess the following properties: Purity of aluminum not less than about 95%, particle size in the range of from 4 to 32 mesh, apparent specific gravity in the range of from 0.85 to 1 and specific surface area in the range of from 0.2 to 1 $m^2/g$ (by the BET method).

The reason for the specific range of the particle size is that the rate of conversion by the dehydrogenation reaction is lower than is economically desirable where the particle size is greater than the upper limit, whereas the bed of the catalyst offers more resistance to the flow of the reactants than is tolerable from the operational point of view where the particle size is smaller than the lower limit. The apparent specific gravity and the specific surface area of aluminum sponge fall in their respectively specified ranges only when the particle size falls in the range specified above.

Then, a noble metal of Group 8 of the Periodic Table of Element is prepared. Examples of noble metals which are usable for this invention include platinum, palladium, rhodium, iridium, ruthenium and osmium. Preferred noble metals are platinum and palladium. The noble metal is desirably prepared in the form of a complex such as, for example, a dinitro-diamine complex.

Now, the method adopted for the preparation of the catalyst will be specifically described. When the noble metal is not in the form of a complex, it is dissolved in an aqueous dinitrodiamine solution to produce an aqueous solution of the noble metal complex of dinitro-diamine. Then ammonia is added to the aqueous solution and the aluminum sponge is placed in the solution. The resultant solution is evaporated to dryness to have the noble metal deposited on the aluminum sponge. When necessary, the aluminum sponge having the noble metal deposited thereon may be calcined at a temperature about 500° C. so as to afford a catalyst with very low friability which can withstand severe conditions.

In the actual practice of the method described above, the noble metal of Group 8 of the Periodic Table of Elements is carried on the aluminum sponge in a ratio of 0.001 to 0.1 part by weight of the noble metal to 1 part of aluminum. Specifically, platinum or palladium is carried preferably in the amount of from 0.005 to 0.01 part by weight on aluminum sponge having 1 part of aluminum.

The catalyst obtained as described above possesses properties ideal for the purpose of catalyzing the dehydrogenation of cyclohexanes. Now, the reaction of dehydrogenation of cyclohexanes by use of the catalyst of the present invention will be described.

The term "cyclohexanes" has been defined herein to refer collectively to cyclohexane and alkyl-substituted cyclohexanes. Alkyl-substituted cyclohexanes which have practical properties to which the melted of the present invention can be effectively applied are those which have at least one alkyl group such as methyl, ethyl, or propyl group. The cyclohexanes are represented by the general formula:

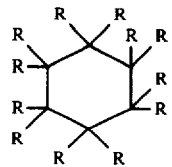

(wherein, every R represents a hydrogen atom in the case of cyclohexane, while up to two R's are each an alkyl group having up to three carbon atoms and the remaining R's are each a hydrogen atom in the case of an alkyl-substituted cyclohexane). The reaction can be carried out effectively in a fixed-bed system or a fluidized-bed system. The catalyst is kept at temperatures of from 290° to 620° C., preferably from about 300° to about 600° C., and the cyclohexanes are brought into contact with the heated catalyst in conjunction with hydrogen, for a period of not less than 0.1 second, preferably not less than 0.5 second. The reaction is completed in a very short time of less than 0.1 second. In the reaction, the hydrogen is desired to be present in an amount of from 10 to 20 mols, preferably from 13.8 to 20 mols, per mol of the cyclohexane.

The reason for the presence of hydrogen in the reaction system is that it prevents the catalyst from degradation of activity. When the amount of the hydrogen present in the reaction system is limited as defined above, the catalyst is prevented from undergoing the phenomenon of carbonization which is responsible for the degradation of activity.

The product of this reaction comprises the dehydrogenation product, hydrogen and the unaltered portion of the cyclohexane. The dehydrogenation product is isolated by low-temperature processing, distillation or some other suitable technique. The hydrogen resulting from the isolation may be used again in the reaction of dehydrogenation by the method of this invention.

By the method of the present invention using the catalyst of this invention, cyclohexanes can be dehydrogenated at a high conversion rate and with high selectivity into corresponding products such as benzene, toluene, xylene and cumene, plus hydrogen as described above. Since the catalyst of this invention uses metallic aluminum of a spongy texture as its carrier and, therefore, enjoys high thermal conductivity, it effectively curbs the decomposition of cyclohexane, otherwise possible secondary reactions.

The method of this invention can be utilized for the principal organic chemical reaction aimed at the production of benzene and hydrogen through the dehydrogenation of cyclohexane. Since this dehydrogenation of cyclohexanes is an endothermic reaction involving the absorption of about 50 Kcal of thermal energy per mol of the cyclohexane under treatment, the method of this invention can use the heat liberated from some other chemical plant in promoting this endothermic reaction of dehydrogenation, so that heat which would otherwise be released into the atmosphere and wasted can be captured as chemical energy and preserved in that form for future use. Thus, the present invention can be utilized as one link in the chain of energy-saving technologies.

Now, the present invention will be described more specifically below with reference to working examples.

EXAMPLE 1:

In an evaporation dish placed over a hot water bath, 0.833 g of dinitrodiamine platinum [(NO$_2$)$_2$(NH$_3$)$_2$Pt] was dissolved in 150 cc of water and 2 cc of an aqueous 28% ammonia solution was added thereto to ensure thorough solution. To the resultant solution which was kept fully agitated, 50.0 g of aluminum sponge (8 to 10 mesh in particle size, about 0.5 m$^2$/g of specific surface area and 0.8 of apparent specific gravity) was added. The resultant mixture was evaporated to dryness, to afford about 5.1 g of Pt-aluminum sponge catalyst containing 1% by weight of platinum.

Then 4.0 g of the catalyst was placed in a quartz glass reaction tube 20 mm in inside diameter and 600 mm in length. A mixed gas composed of hydrogen and cyclohexane in a molar ratio of 13.8:1 was passed over the catalyst, with the contact time fixed at 3.6 seconds and the reaction temperature at 550° C., to effect dehydrogenation of cyclohexane. The same procedure was repeated by using methyl cyclohexane in place of cyclohexane. Consequently, nearly 100% of the cyclohexane was dehydrogenated into benzene and about 94% of the methyl cyclohexane into toluene without entailing any discernible secondary reaction.

Comparative Example 1:

Using the same reaction tube, cyclohexane and methyl cyclohexane were dehydrogenated by following the procedure of Example 1 except that a typical commercially available Pt-alumina type catalyst (containing 1% by weight of platinum and having 0.9 of bulk density and 200 m$^2$/g of specific surface area) was used in the place of the catalyst of the present invention. Although both cyclohexane and methyl cyclohexane were substantially completely converted, the former dehydrogenation product consisted of 60 to 70% of benzene with the balance composed of decomposition and polymerization products and the latter dehydrogenation product consisted of 40 to 50% of toluene with the balance composed similarly of decomposition and polymerization products.

EXAMPLE 2

By the procedure of Example 1, about 46.6 g of a Pd-aluminum sponge catalyst (containing 1% by weight of palladium) was prepared by using 1.0 g of dinitrodiamine palladium [(NO$_2$)$_2$(NH$_3$)$_2$Pd] and 45.56 g of aluminum sponge (8 to 10 mesh in particle size, about 0.5 m$^2$/g of specific surface area and 0.8 of apparent specific gravity). Similarly as in the procedure of Example 1, cyclohexane and methyl cyclohexane were dehydrogenated using the catalyst. Consequently, nearly 100% of the cyclohexane was dehydrogenated into benzene and 90% of the methyl cyclohexane into toluene without entailing any discernible secondary reaction.

EXAMPLE 3

Using the same Pt-aluminum sponge catalyst, cyclohexane and methyl cyclohexane were dehydrogenated following the procedure of Example 1, with the sole exception of the reaction temperature which was fixed at 300° C. Consequently, 70% of the cyclohexane was dehydrogenated and substantially completely converted into benzene and 92% of the methyl cyclohexane was dehydrogenated and substantially completely, converted into toluene, without entailing any discernible secondary reaction.

EXAMPLE 4

By the procedure of Example 1, about 50.4 g of a Pt-aluminum sponge catalyst (containing 0.41% by weight of platinum) was prepared by using 0.35 g of dinitrodiamine platinum and 50.0 g of aluminum sponge (8 to 10 mesh in particle size, about 0.5 m$^2$/g of specific surface area and 0.8 g of apparent specific gravity). Similarly as in the procedure of Example 1, cyclohexane was dehydrogenated by using the catalyst. Consequently, 60% of the cyclohexane was dehydrogenated and was substantially completely converted into benzene without entailing any discernible secondary reaction.

EXAMPLE 5

Cyclohexane was dehydrogenated by following the procedure of Example 1 using the same Pt-aluminum sponge catalyst, except that the contact time was fixed at 0.9 second. Consequently, 90% of the cyclohexane was dehydrogenated and was substantially completely converted into benzene without entailing any discernible secondary reaction.

EXAMPLE 6

(A) 1,2-Dimethyl cyclohexane, (B) 1,3-dimethyl cyclohexane, (C) 1,4-dimethyl cyclohexane, (D) ethyl cyclohexane and (E) isopropyl cyclohexane were dehydrogenated by following the procedure of Example 1 using the same Pt-aluminum sponge catalyst, except that the reaction temperature was fixed at 475° C. Consequently, 91% of (A), 76% of (B), 89% of (C), 92% of (D) and 61% of (E) were dehydrogenated and were substantially completely converted into o-xylene in the case of (A), n-xylene in the case of (B), p-xylene in the case of (C), ethylbenzene in the case of (D) and cumene in the case of (E) respectively without entailing any discernible secondary reaction.

Comparative Example 2:

1,3-Dimethyl cyclohexane was dehydrogenated by following the procedure of Example 1, except that the Pt-alumina catalyst (containing 1% by weight of platinum) of Comparative Example 1 was used and the reaction temperature was fixed at 475° C. Although nearly 100% of the 1,3-dimethyl cyclohexane was dehydrogenated, the reaction mixture consisted of 20 to 25% of m-xylene and the balance composed of decomposition and polymerization products.

What is claimed is:

1. A method for dehydrogenation of cyclohexane and alkyl-substituted cyclohexanes, which comprises bringing at least one compound selected from the group consisting of cyclohexane and alkyl-substituted cyclohexanes into contact with a catalyst which comprises an aluminum sponge and a noble metal of Group 8 of the Periodic Table of the Elements carried on said aluminum sponge; in conjunction with hydrogen; at temperatures of from 290° to 620° C.

2. The method according to claim 1, wherein the amount of hydrogen is not less than 13.8 mols per mol of cyclohexane or alkyl-substituted cyclohexane under treatment.

* * * * *